US005670325A

United States Patent [19]
Lapidus et al.

[11] Patent Number: 5,670,325
[45] Date of Patent: Sep. 23, 1997

[54] METHOD FOR THE DETECTION OF CLONAL POPULATIONS OF TRANSFORMED CELLS IN A GENOMICALLY HETEROGENEOUS CELLULAR SAMPLE

[75] Inventors: Stanley N. Lapidus, Bedford, N.H.; Anthony P. Shuber, Milford; Kevin M. Ulmer, Cohasset, both of Mass.

[73] Assignee: Exact Laboratories, Inc., Maynard, Mass.

[21] Appl. No.: 700,583

[22] Filed: Aug. 14, 1996

[51] Int. Cl.⁶ .................................................. C12Q 1/68
[52] U.S. Cl. .................................................. 435/6
[58] Field of Search .......................... 435/6, 7.2, 91.1, 435/91.3, 240.2, 252.3, 254.11

[56] References Cited

U.S. PATENT DOCUMENTS

| | | | |
|---|---|---|---|
| 4,101,279 | 7/1978 | Aslam | 422/99 |
| 4,309,782 | 1/1982 | Paulin | 4/661 |
| 4,333,734 | 6/1982 | Fleisher | 436/66 |
| 4,445,235 | 5/1984 | Slover et al. | 4/144.2 |
| 4,535,058 | 8/1985 | Weinberg et al. | 435/6 |
| 4,683,195 | 7/1987 | Mullis et al. | 435/6 |
| 4,705,050 | 11/1987 | Markham | 128/749 |
| 4,735,905 | 4/1988 | Parker | 436/174 |
| 4,786,718 | 11/1988 | Weinberg et al. | 530/387.7 |
| 4,857,300 | 8/1989 | Maksem | 435/40.51 |
| 4,871,838 | 10/1989 | Bos et al. | 536/24.31 |
| 4,981,783 | 1/1991 | Augenlicht | 435/6 |
| 4,982,615 | 1/1991 | Sultan et al. | 73/864.51 |
| 5,087,617 | 2/1992 | Smith | 514/44 |
| 5,126,239 | 6/1992 | Livak et al. | 435/6 |
| 5,137,806 | 8/1992 | LeMaistre et al. | 435/6 |
| 5,149,506 | 9/1992 | Skiba et al. | 422/102 |
| 5,196,167 | 3/1993 | Guadagno et al. | 422/56 |
| 5,248,671 | 9/1993 | Smith | 514/44 |
| 5,272,057 | 12/1993 | Smulson et al. | 435/6 |
| 5,330,892 | 7/1994 | Vogelstein et al. | 435/6 |
| 5,331,973 | 7/1994 | Fiedler et al. | 128/760 |
| 5,348,855 | 9/1994 | Dattagupta et al. | 435/6 |
| 5,352,775 | 10/1994 | Albertsen et al. | 536/23.1 |
| 5,362,623 | 11/1994 | Vogelstein et al. | 435/6 |
| 5,369,004 | 11/1994 | Polymeropoulos et al. | 435/6 |
| 5,378,602 | 1/1995 | Polymeropoulos et al. | 435/6 |
| 5,380,645 | 1/1995 | Vogelstein | 435/6 |
| 5,380,647 | 1/1995 | Bahar | 435/7.23 |
| 5,382,510 | 1/1995 | Levine et al. | 435/6 |
| 5,409,586 | 4/1995 | Kamahori et al. | 204/452 |
| 5,458,761 | 10/1995 | Kamahori et al. | 204/602 |
| 5,463,782 | 11/1995 | Carlson et al. | 4/661 |
| 5,466,576 | 11/1995 | Schulz et al. | 435/6 |
| 5,468,610 | 11/1995 | Polymeropoulos et al. | 435/6 |
| 5,468,613 | 11/1995 | Erlich et al. | 435/6 |
| 5,489,508 | 2/1996 | West et al. | 435/6 |
| 5,492,808 | 2/1996 | de la Chapelle et al. | 435/6 |
| 5,496,470 | 3/1996 | Lenhart | 210/222 |
| 5,508,164 | 4/1996 | Kausch et al. | 435/6 |
| 5,512,441 | 4/1996 | Ronai | 435/6 |
| 5,514,547 | 5/1996 | Balazs et al. | 435/6 |
| 5,527,676 | 6/1996 | Vogelstein et al. | 435/6 |
| 5,532,108 | 7/1996 | Vogelstein | 435/240.2 |

FOREIGN PATENT DOCUMENTS

| | | |
|---|---|---|
| A-11325/95 | 10/1994 | Australia. |
| 0 284 362 A2 | 9/1988 | European Pat. Off.. |
| 0 337 498 | 10/1989 | European Pat. Off.. |
| 0 390 323 A2 | 1/1990 | European Pat. Off.. |
| 0 390 323 A3 | 1/1990 | European Pat. Off.. |
| 0 407 789 A1 | 1/1991 | European Pat. Off.. |
| 0 407 789 B1 | 1/1991 | European Pat. Off.. |
| 0 608 004 A2 | 7/1994 | European Pat. Off.. |
| 0 259 031 B1 | 11/1994 | European Pat. Off.. |
| WO92/13103 | 8/1992 | WIPO. |
| WO93/20233 | 10/1993 | WIPO. |
| WO94/00603 | 1/1994 | WIPO. |
| WO94/10575 | 5/1994 | WIPO. |
| WO95/07361 | 3/1995 | WIPO. |
| WO95/09928 | 4/1995 | WIPO. |
| WO95/12606 | 5/1995 | WIPO. |
| WO95/13397 | 5/1995 | WIPO. |
| WO95/15400 | 6/1995 | WIPO. |
| WO95/16792 | 6/1995 | WIPO. |
| WO95/19448 | 7/1995 | WIPO. |
| WO95/18818 | 7/1995 | WIPO. |
| WO95/25813 | 9/1995 | WIPO. |
| WO95/31728 | 11/1995 | WIPO. |
| WO96/01907 | 1/1996 | WIPO. |
| WO96/08514 | 3/1996 | WIPO. |
| WO96/06951 | 3/1996 | WIPO. |
| WO96/12821 | 5/1996 | WIPO. |
| WO96/13611 | 5/1996 | WIPO. |

OTHER PUBLICATIONS

Sanger F., S. Nicklen and A.R. Coulson (Dec. 1977) "DNA sequencing with chain-terminating inhibitors" vol. 74, No. 12 *Proc. Natl. Acad. Sci. USA* pp. 5463–5467.

Wallace R.B., et al. (1979) "Hybridization of synthetic oligodeoxyribonucleotides to Φχ 174 DNA: the effect of single base pair mismatch" vol. 6, No. 11 *Nucleic Acids Research* pp. 3543–3557.

Coll P., K. Phillips, and F. C. Tenover (Oct. 1989) "Evaluation of a Rapid Method of Extracting DNA from Stool Samples for Use in Hybridization Assays" vol. 27, No. 10 *Journal of Clinical Microbiology* pp. 2245–2248.

Jessup J. M. and G. E. Gallick (Sep./Oct. 1992) "The Biology of Colorectal Carcinoma" *Current Problems in Cancer* pp. 263–328.

Litia A., L. Liukkonen and H. Siitari (1992) "Simultaneous detection of two cystic fibrosis alleles using dual-label time-resolved fluorometry" 6 *Molecular and Cellular Probes* pp. 505–512.

(List continued on next page.)

*Primary Examiner*—James Ketter
*Assistant Examiner*—Irem Yucel
*Attorney, Agent, or Firm*—Testa, Hurwitz & Thibeault, LLP

[57] ABSTRACT

Methods are provided for detecting the presence of mutant sequences in a subpopulation of gene sequences in a biological sample. These methods are particularly useful for identifying individuals with gene mutations indicative of early colorectal cancer.

38 Claims, 5 Drawing Sheets

OTHER PUBLICATIONS

Young G. P., and B. H. Demediu (1992) "The genetics, epidemiology, and early detection of gastrointestinal cancers" 4 *Current Opinion in Oncology* pp. 728–735.

Hoss M., et al. (Sep. 17, 1992) "Excrement analysis by PCR" *Scientific Correspondence* pp. 199.

Sidransky, et al. (Apr. 3, 1992) "Identification of ras Oncogene Mutations in the Stool of Patients with Curable Colorectal Tumors" vol. 256 *Science* pp. 102–105.

Takeda S., S. Ichii, and Y. Nakamura (1993) "Detection of K–ras Mutation in Sputum by Mutant–Allele–Specific Amplification (MASA)" 2 *Human Mutation* pp. 112–117.

Leong P. K., et al. (1993) "Detection of MYCN Gene Amplification and Deletions of Chromosome 1p in Neuroblastoma by In Situ Hybridization Using Routine Histologic Sections" vol. 69, No. 1 *Laboratory Investigations* pp. 43–50.

Thibodeau S.N., G. Bren, D. Schaid (May 7, 1993) "Microsatellite Instability in Cancer of the Proximal Colon" vol. 260 *Science* pp. 816–819.

Naber S. P.(Dec. 1, 1994) "Molecular Pathology—Detection of Neoplasia" 331 *New England Journal of Medicine* pp. 1508–1510.

Cave H., et al. (1994) "Reliability of PCR Directly from Stool Samples: Usefulness of an Internal Standard" vol. 16, No. 5 *Bio Techniques* pp. 809–810.

Caldas C., et al (Jul. 1, 1994) "Detection of K–ras Mutations in the Stool of Patients with Pancreatic Adenocarcinoma and Pancreatic Ductal Hyperplasia" 54 *Cancer Research* pp. 3568–3573.

Charlesworth B., P. Sniegowski and W. Stephan (Sep. 15, 1994) "The evolutionary dynamics of repetitive DNA in eukaryotes" vol. 371 *Native* pp. 215–220.

Fearon E. R.(1995) "16 Molecular Abnormalities in Colon and Rectal Cancer" *The Molecular Basis of Cancer* pp. 340–357.

Ravelingien N., J. C. Pector & T. Velu (1995) "Contribution of molecular oncology in the dection of colorectal carcinomas" 58 *Acta Gastro–Enterologica Belgica* pp. 270–273.

Duffy M.J.(1995) "Can Molecular Markers Now Be Used for Early Diagnosis of Malignancy?" 41/10 *Clin. Chem.* pp. 1410–1413.

Blum H.E.(1995) "Colorectal Cancer: Future Population Screening for Early Colorectal Cancer" vol. 31 A *European Journal of Cancer,* pp. 1369–1372.

Ridanpaa M., S. Anttila and K. Husgafvel–Pursiainen (1995) "Detection of Loss of Heterozygosity in the p53 Tumor Suppressor Gene Using a PCR–based Assay" 191 *Path. Res. Pract.* pp. 399–402.

Smith–Ravin J., J. England, I.C. Talbot, W. Bodmer (1995) "Detection of c–Ki–ras mutations in faecal samples from sporadic colorectal cancer patients" 36 *Gut* pp. 81–86.

Orlow I., et al., (Oct. 18, 1995) "Deletion of the p16 and p15 Genes in Human Bladder Tumors " vol. 87, No. 20 *Journal of the National Cancer Institute* pp. 1524–1529.

Hasegawa, Y., et al., (1995) "Detection of K–ras mutations in DNAs isolated from feces of patients with colorectal tumors by mutant–allele–specific amplificaiton (MASA)" 10 *Oncogene* pp. 1441–1445.

Loktionov A. and I. K. O'Neill (1995) "Early detection of cancer–associated gene alterations in DNA isolated from rat feces during intestinal tumor induction with 1,2–dimethylhydrazine" 6 *International Journal of Oncology* pp. 437–445.

Honchel R., K. C. Halling and S. N. Thibodeau (1995) "Genomic instability in neoplasia" vol. 6 *Seminars in Cell Biology* pp. 45–52.

Deuter R., S. Pietsch, S. Hertel and O. Muller (1995) "A method for preparation of fecal DNA suitable for PCR" vol. 23, No. 18 *Nucleic Acids Research* pp. 3800–3801.

Dib C., et al. (Mar. 14, 1996) "A comprehensive genetic map of the human genome based on 5,264 microsatellites" vol. 380 *Nature* pp. 152–154.

Cunningham C. and M.G. Dunlop (1996) "Molecular genetic basis of colorectal cancer susceptibility" 83 *British Journal of Surgery* pp. 321–329.

Mao L., et al. (Feb. 2, 1996) "Molecular Detection of Primary Bladder Cancer by Microsatellite Analysis" vol. 271 *Science* pp. 659–662.

Villa E., et al. (May 1996) "Identification of Subjects at Risk for Colorectal Carcinoma Through a Test Based on K–ras Determination in the Stool" vol. 110, No. 5 *Gastroenterology* pp. 1346–1353.

Nollau P., C. Moser, G. Weinland, and C. Wagener (1996) "Detection of K–ras Mutations in Stools of Patients with Colorectal Cancer by Mutant–enriched PCR" 66 *Int. J. Cancer* pp. 332–336.

Eguchi S., N. Kohara, K. Komuta, and T. Kanematsu (Apr. 15, 1996)"Mutations of the p53 Gene in the Stool of Patients with Resectable Colorectal Cancer" vol. 77, No. 8 *Cancer Supplement* pp. 1707–1710.

Nollau P., C. Moser, and C. Wagener (May 1996) "Isolation of DNA from Stool and Bodily Fluids for PCR Amplication" vol. 20, No. 5 *BioTechniques* pp. 784–788.

Rhyu M. S. (Mar. 6, 1996) "Molecular Mechanisms Underlying Hereditary Nonpolyposis Colorectal Carcinoma" vol. 88, No. 5 *Journal of the National Cancer Institute* pp. 240–251.

Gyllensten U. B., Allen M. (1995) "Sequencing of In Vitro Amplified DNA" In *Recombinant DNA Methodology II* (Wu, ed) pp. 565–578.

Iitarä et al. 1992 Molecular and Cellular Probes 6:505–512.

M

1:                             3'ACGCTACGG5'
2:           5'....ATCGGCTTACTGCGATGCC....3'

3:        3'....TAGCCGAATGACGCTACGG....5'
4:            5'ATCGGCTTA3'

F

1:                             3'ACGCTACGG5'
2:           5'....ATCGGCTTATTGCGATGCC....3'

3:        3'....TAGCCGAATAACGCTACGG....5'
4:            5'ATCGGCTTA3'

FIG. 3

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..9
        ( D ) OTHER INFORMATION: /note= "M1"

( x i ) SEQUENCE DESCRIPTION: SEQ ID NO:1:

GGCATCGCA        9

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..19
        ( D ) OTHER INFORMATION: /note= "M2"

( x i ) SEQUENCE DESCRIPTION: SEQ ID NO:2:

ATCGGCTTAC TGCGATGCC        19

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..19
        ( D ) OTHER INFORMATION: /note= "M3"

( x i ) SEQUENCE DESCRIPTION: SEQ ID NO:3:

GGCATCGCAG TAAGCCGAT        19

( 2 ) INFORMATION FOR SEQ ID NO:4:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..9
        ( D ) OTHER INFORMATION: /note= "M4"

( x i ) SEQUENCE DESCRIPTION: SEQ ID NO:4:

ATCGGCTTA        9

( 2 ) INFORMATION FOR SEQ ID NO:5:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..9
        ( D ) OTHER INFORMATION: /note= "F1"

( x i ) SEQUENCE DESCRIPTION: SEQ ID NO:5:

GGCATCGCA        9

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..19
        ( D ) OTHER INFORMATION: /note= "F2"

( x i ) SEQUENCE DESCRIPTION: SEQ ID NO:6:

ATCGGCTTAT TGCGATGCC        19

( 2 ) INFORMATION FOR SEQ ID NO:7:

```
( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i x ) FEATURE:
    ( A ) NAME/KEY: misc_feature
    ( B ) LOCATION: 1..19
    ( D ) OTHER INFORMATION: /note= "F3"

( x i ) SEQUENCE DESCRIPTION: SEQ ID NO:7:

GGCATCGCAA TAAGCCGAT                                              19

( 2 ) INFORMATION FOR SEQ ID NO:8:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1..9
        ( D ) OTHER INFORMATION: /note= "F4"

( x i ) SEQUENCE DESCRIPTION: SEQ ID NO:8:

ATCGGCTTA                                                          9
```

METHOD FOR THE DETECTION OF CLONAL POPULATIONS OF TRANSFORMED CELLS IN A GENOMICALLY HETEROGENEOUS CELLULAR SAMPLE

FIELD OF THE INVENTION

This invention relates to methods useful for disease diagnosis by detecting the presence of genetic mutations, including deletions, in cellular samples containing a small amount of mutated genetic material dispersed within a major amount of diagnostically-irrelevant (normal) genetic material. Methods of the invention are especially useful in the detection of genetic mutations characteristic of cancer.

BACKGROUND OF THE INVENTION

Cancer is a disease characterized by genomic instability. Generally, genomic instability defines a broad class of disruptions in genomic nucleotide sequences. Such disruptions include the loss of heterozygosity (usually characterized by massive loss of chromosomal DNA), microsatellite instability (usually indicative of defects in DNA repair mechanisms), and mutations (which include insertions, deletions, substitutions, duplications, rearrangements, or modifications). Numerous genomic instabilities have been associated with cancer. For example, mutations in a number of oncogenes and tumor suppressor genes have been implicated in tumorigenesis. Duffy, *Clin. Chem.*, 41:1410–1413 (1993). In addition, the loss of heterozygosity at the P53 tumor suppressor locus has been correlated with various types of cancer. Ridanpaa, et al., *Path. Res. Pract*, 191:399–402 (1995). The loss or other mutation of the apc and dcc tumor suppressor genes has also been associated with tumor development. Blum, *Europ. J. Cancer*, 31A:1369–372 (1995). Finally, tumorigenesis has also been correlated with microsatellite instability.

Genetic changes characteristic of genomic instability theoretically can serve as markers for the early stages of, for example, colon cancer, and can be detected in DNA isolated from biopsied colonic epithelium and in some cases from transformed cells shed into fecal material. Sidransky, et al., *Science*, 256:102–105 (1992).

Detection methods proposed in the art are time-consuming and expensive. Duffy, supra. Moreover, methods according to the art cannot be used to identify a loss of heterozygosity or microsatellite instability in small subpopulation of cells when the cells exist in a heterogeneous (i.e., clonally impure) sample. For example, in U.S. Pat. No. 5,527,678, it is stated that tissue samples in which a mutation is to be detected should be enriched for tumor cells in order to detect the loss of heterozygosity in a p53 gene.

Techniques, such as PCR, have been used to detect a loss of heterozygosity resulting from massive deletions characteristic of late-stage adenomas. See, e.g., U.S. Pat. No. 5,330,892. Such techniques generally require the use of large numbers of primer pairs, and they will not work at all in a heterogeneous sample. A recent publication reports the use of PCR and ELISA techniques to perform quantitative analysis of mutations in early-stage tumors. U.S. Pat. No. 5,512,441. Identification of an abnormal subpopulation of cells in a heterogeneous sample of mostly normal cells and cellular debris, which subpopulation is characterized by loss of heterozygosity or microsatellite instability, is even more difficult because such detection involves the identification of a subpopulation of nucleotide fragments that are difficult to distinguish from the sea of heterogeneous normal cellular material in which they exist. A further problem is that mutation at any locus of a growing number of different oncogenes or tumor suppressor genes can result in cancer, and a screening approach capable of scanning all or even most loci in these genes is not currently available.

Microsatellite instability may also be a marker for cancer. Microsatellites are dispersed throughout the genome at an average frequency of about 1 in 100,000 base pairs. They comprise tandem or trinucleotide repeats that normally are inherited in a stable fashion. See, e.g., Charlesworth, et al., *Nature*, 371:215–220 (1994). While these sequences perform no known function in the genome, many of them have been mapped and have been used as markers based upon their sequence length polymorphisms. Clonal changes in microsatellite DNA associated with defects in mismatch repair pathways are thought to be suitable markers for hereditary non-polyposis colorectal cancer (HNPCC). In HNPCC tumor samples, for example, Microsatellites were found to have multiple insertions and/or deletions. Microsatellite instability may be an effective marker for failure of mismatch repair in oncogenes or in tumor suppressor genes. While microsatellite instability itself is not indicative of cancer, it is evidence that mutations may occur in regions that are critical for onset of cancer. It follows that detection of instability in Microsatellites indicates that the patient is at risk of developing a clonal subpopulation of cancer cells.

Colorectal cancer is a common cause of death in Western society. Any tumor or precancerous polyp that develops along the length of the colon or the rectum sheds cells or DNA from cells into the lumen of the colon. Shed cells or cellular DNA are usually incorporated on stool as stool passes through the colon. In the early stages of cancer, cancerous or precancerous cells represent a very small fraction of the shed epithelial cells or DNA in stool. Current methods for detection of colorectal cancer do not focus on detecting cancerous or precancerous cells in stool. Rather, such methods typically focus on extracellular indicia of the presence of cancer, such as the presence of fecal occult blood or carcinoembryonic antigen circulating in serum.

It is known, however, that both sporadic and hereditary colorectal cancers result from mutations in oncogenes and tumor suppressor genes. Such mutations appear to occur at a point in the etiology of the disease that is much earlier than the point at which extracellular indicia or clinical signs of cancer are observed. If detected early, colon cancer may be effectively treated by surgical removal of the cancerous tissue. Surgical removal of early-stage colon cancer is usually successful because colon cancer begins in cells of the colonic epithelium and is isolated from the general circulation until the occurrence of invasion through the epithelial lining. Thus, detection of early mutations in colorectal cells would greatly increase survival rate.

Current non-invasive methods for detection of colon cancer involve the detection of fecal occult blood and carcinoembryonic antigen. These screening methods often either fail to detect colorectal cancer or they detect colorectal cancer only after it has progressed to an untreatable stage. Moreover, carcinoembryonic antigen is thought not to be an effective predictor of cancer but merely an indicator of recurrent cancer.

Invasive techniques, such as endoscopy, while effective, are expensive and painful and suffer from low patient compliance. Accordingly, current colon cancer screening methods are not practical for screening large segments of the population. See, e.g., Blum, *Europ. J. Cancer*, 31A:1369–1372 (1995).

Therefore, there is a need in the art for simple and efficient non-invasive methods for reliable large-scale screening to identify individuals with early stage colon cancer. Such methods are provided herein.

SUMMARY OF THE INVENTION

The present invention provides methods for detecting a subpopulation of genomically transformed cells or cellular debris. Such methods detect the presence in a biological sample of a clonal subpopulation of cells which have a genome different from that of the wild type, and from bacterial, parasitic, or contaminating organisms that may also be present in the sample. Practice of the invention permits, for example, detection of a trace amount of DNA derived from cancer or precancer cells in a biological sample containing a majority of "normal" DNA or whole cells. A preferred use of the methods is to reliably detect in a stool sample voided by a patient the presence of a trace amount of cells and/or cellular debris containing DNA shed into the colon at the site of an asymptomatic precancerous or cancerous lesion. The invention takes advantage of several important insights which permit, for example, reliable detection of a DNA deletion at a known genomic site characteristic of a known cancer cell type.

In general, the invention comprises the comparative measurement of two genomic sequences. One genomic sequence is stable through transformation, (i.e., it is identical in both malignant and wild type cells in the sample). A second genomic sequence typically undergoes change during the course of transformation (i.e., it is mutated during the development of malignant precursor cells). Hybridization probes are used to detect the presence of each genomic sequence. If the number of hybridization events involving the two genomic sequences is different, the difference may be due to insignificant background or it may be due to a statistically-significant difference in the quantities of the two genomic sequences in the population from which the sample was drawn. In the latter case, the difference can be correlated, to a degree of defined statistical confidence, with the presence in the sample of a subpopulation of cells having an altered (i.e., non-wild type) genomic sequence.

The invention may be divided into three general embodiments. (1) In a first general embodiment, a quantitative amount (number of copies) of a gene or gene fragment of interest in a sample (i.e. a gene the mutation of which is known or suspected to be associated with cancer) is compared to a quantitative amount of a reference gene or gene fragment in the sample, the reference gene being a gene which is not normally associated with cancer and which normally has a low rate of mutation. A statistically-significant difference between the two quantitative amounts is indicative of genomic instability in a cellular subpopulation in the sample. (2) In a second general embodiment of the invention, a quantitative amount of a region on a maternal allele is compared to a quantitative amount of the corresponding region on a paternal allele. A statistically-significant difference between the two quantitative amounts is indicative of genomic instability. (3) In a third general embodiment, the number of microsatellite repeats at a particular locus are compared between maternal and paternal alleles. A statistically-significant difference in those numbers is indicative of an error in the mismatch repair mechanisms in a subpopulation of cells in the sample or may indicate that allelic loss has taken place. As stated above, errors in mismatch repair may result in mutations in tumor suppressor genes or in oncogenes. Cancer detection in any of the three embodiments of the invention is achieved by measuring the number of hybridizations between at least two different nucleotide probes and their respective genomic sequences.

One feature of the invention is that it has now been recognized that materials from cells lining the colon (e.g., a polyp or lesion) are shed onto forming stool only in a region comprising a longitudinal stripe along the length of the stool. Thus, unless the stool sample under investigation is a whole stool or comprises at least a cross-section of a stool, the sample will contain the relevant diagnostic information only by chance. The colon contains numerous bends and folds throughout its length. See, U.S. patent application Ser. No., 08/699,678 (Atty. Docket No. EXT-002), filed on even date herewith. Epithelial cells lining the colon normally migrate from a basal position in colonic crypts, where stem cells divide by mitosis, to the top of the crypts and are then shed into the lumen. Colonic epithelial cells that line the intestinal lumen typically undergo regeneration every four to five days as a result of the rapid turnover rate through the epithelium. Accordingly, sloughed epithelial cells or their DNA are constantly being deposited in the forming stool as it passes through the lumen. As the stool proceeds toward the rectum and becomes progressively more solid (from an initial liquid state), epithelial cells are only sloughed onto the portion of the stool making contact with the portion of the lumen that formerly contained those cells in its epithelial lining. Epithelial cells of a polyp (a polyp is a pre-cancerous growth; while not all polyps become cancerous, almost all cancers arise from polyps) undergo the same rapid life cycle and shedding described above for normal colonic epithelial cells. Accordingly, cells shed from polyps are typically only absorbed onto the surface of the forming stool that makes contact with the polyp. However, if the stool is in a liquid state, mixing of shed polyp cells throughout the stool occurs automatically.

Accordingly, the present invention provides methods for detecting genomic changes in a subpopulation of cells in a sample of biological material. Methods of the invention are useful for the detection of changes in the nucleotide sequence of an allele in a small subpopulation of cells present in a large, heterogeneous sample of diagnostically-irrelevant biological material. Methods of the invention are useful for the detection and diagnosis of a genetic abnormality, such as a loss of heterozygosity or, more generally, a mutation, which can be correlated with a disease, such as cancer. For purposes of the present invention, unless the context requires otherwise, a "mutation" includes modifications, rearrangements, deletions, substitutions, and additions in a portion of genomic DNA or its corresponding mRNA.

In a preferred embodiment, the invention provides methods for detecting a clonal subpopulation of transformed cells contained in, or suspected of being contained in, a biological sample obtained from an organism, such as a human. The methods comprise the steps of determining from the biological sample a number X of a first wild-type polynucleotide that is known or suspected not to be mutated in either wild-type cells or in transformed cells. A further step comprises determining from the biological sample a number Y of a second wild-type polynucleotide suspected of being mutated in a subpopulation of cells in the biological sample. Then, one determines whether a statistically-significant difference exists between X and Y. In a normal sample there is no mutation and so there is no statistically-significant difference between the number of each of the somatic genes in a normal cell. As a result, X and Y are not different from each other in a statistically significant sense. In contrast, the presence of a statistically significant difference between X and Y is indicative of the presence of a clonal subpopulation of transformed cells in the biological sample embodying a mutation. Statistical significance may be determined by any method known in the art. However, no formal measurement of statistical significance need be performed in connection with any given assay. Rather, assays are designed to detect a large enough number of binding events such that at least a threshold difference between the numbers is dispositive of the issue of the presence of a mutant subpopulation of cells at any desired level of certainty.

Also, in a preferred embodiment, transformed cells sought to be detected using methods according to the invention are malignant cells. Transformed cells detected according to methods of the invention may be induced transformants, transformed, for example, by a virus, by radiation, or by chemical or other carcinogenic means. Methods of the invention may be performed on any biological sample, including tissue and body fluid samples. Particularly preferred biological samples include pus, sputum, semen, blood, saliva, cerebrospinal fluid, and urine. In an important embodiment of the invention the sample is stool which is analyzed to detect colorectal cancer or precancer. Methods of the invention may be practiced by exposing the biological sample to one or more oligonucleotide probes in order to separately detect the number X of a first polynucleotide and the number Y of a second polynucleotide. Probes for use in the invention are detectably labeled. Preferred labels include fluorescent labels attached, for example, by affinity binding pairs (such as carbohydrate/lectin or avidin/biotin). Highly-preferred labels are microscopic particles which are counted by a detection apparatus, preferably a high-speed electronic apparatus as disclosed herein. The numbers X and Y are preferably proportional and most preferably equal to the number of target polynucleotide detection events occurring in the biological sample.

Methods of the invention are especially useful for the detection of colorectal cancer or precancerous cells in humans. For purposes of the present invention, precancerous cells are cells that have a mutation that is associated with cancer, and which renders such cells susceptible to becoming cancerous. Such methods comprise determining whether cells or nucleotide debris in a stool sample include a deletion of a polynucleotide normally present in a wild-type genome of the human or other mammal. The sample may be exposed to a plurality of first and second oligonucleotide probes under hybridization conditions, thereby to hybridize (i) first probe to copies of a first polynucleotide segment characteristic of a wild-type genomic region known or suspected not to be deleted in cells of the sample and (ii) second probe to copies of a second polynucleotide segment characteristic of the wild-type genomic region suspected of being mutated in the sample. The number of duplexes formed with each of the first and second probes is then detected and counted. The presence of a statistically-significant difference in those two numbers is indicative of the presence in the sample of a mutation that may be characteristic of colorectal cancer. Endoscopy or other visual examination procedures are then indicated.

In a preferred embodiment, probes are labeled with beads or particles. In this embodiment, probes used for detection of genomic polynucleotide segments in a sample are preferably bound to such beads in a ratio of one probe to one bead, and the beads linked to the first and second probes are distinguishable, for example, by size. Use of such hybridization beads or particles facilitates the quantitative detection of genomic polynucleotide segments in the sample using, for example, an impedance counter, such as a "Coulter counter".

Methods according to the invention also may be used to detect a loss of heterozygosity at an allele by determination of the amounts of maternal and paternal alleles comprising a genetic locus that includes at least one single-base polymorphism. A statistically-significant difference in the amounts of each allele is indicative of a mutation in an allelic region encompassing the single-base polymorphism. In this method, a region of an allele comprising a single-base polymorphism is identified, using, for example, a database, such as GenBank, or by other means known in the art. Probes are designed to hybridize to corresponding regions on both paternal and maternal alleles immediately 3' to the single base polymorphism as shown in FIG. 3. After hybridization, a mixture of at least two of the four common dideoxy nucleotides are added to the sample, each labeled with a different detectable label. A DNA polymerase is also added. Using allelic DNA adjacent the polymorphic nucleotide as a template, hybridized probe is extended by the addition of a single dideoxynucleotide that is the binding partner for the polymorphic nucleotide. After washing to remove unincorporated dideoxynucleotides, the dideoxy-nucleotides which have been incorporated into the probe extension are detected by determining the number of bound extended probes bearing each of the two dideoxy nucleotides in, for example, a flow cytometer or impedance counter. The presence of an almost equal number of two different labels mean that there is normal heterozygosity at the polymorphic nucleotide. The presence of a statistically-significant difference between the detected numbers of the two labels means that a deletion of the region encompassing the polymorphic nucleotide has occurred in one of the alleles.

Methods of the invention may be used to determine whether a patient is a candidate for follow-up invasive diagnostic or other procedures, such as endoscopy. For example, methods of the invention may be used to detect a mutation in a tumor suppressor gene or an oncogene in a subpopulation of cells in a stool sample obtained from a patient. An endoscopy procedure may then be performed on patients diagnosed with a mutation. A positive endoscopy result is then followed by polypectomy, surgery, or other treatment to remove cancerous or precancerous tissue.

Accordingly, it is an object of the invention to provide methods for detecting genomic instability in a subpopulation of cells in a cellular sample. It is a further object of the invention to provide methods for detecting a genomic change in a subpopulation of cells, wherein the genomic change is indicative of cancer. It is another object of the invention to detect a loss of heterozygosity in a genomic region associated with cancer, such as a tumor suppressor region. It is yet another object of the invention to provide methods for detecting heterozygosity and the loss thereof at single-base polymorphic nucleic acids. Finally, it is an object of the invention to provide methods for the detection of cancer, and particularly colorectal cancer by detection of cells or cellular debris indicative of cancer in a heteogeneous sample, such as a stool sample.

Further aspects of the invention will become apparent upon consideration of the following detailed description and of the drawings.

DESCRIPTION OF THE DRAWINGS

FIG. 3 shows four possible probe attachment sites on allelic regions characterized by having a single base polymorphism. In FIG. 3, sequence M1 is SEQ ID NO:1; sequence M2 is SEQ ID NO:2; sequence M3 is SEQ ID NO:3; sequence M4 is SEQ ID NO:4; sequence F1 is SEQ ID NO:5; sequence F2 is SEQ ID NO: 6; sequence F3 is SEQ ID NO:7; sequence F4 is SEQ ID NO:8.

DETAILED DESCRIPTION OF THE INVENTION

Figure 1:
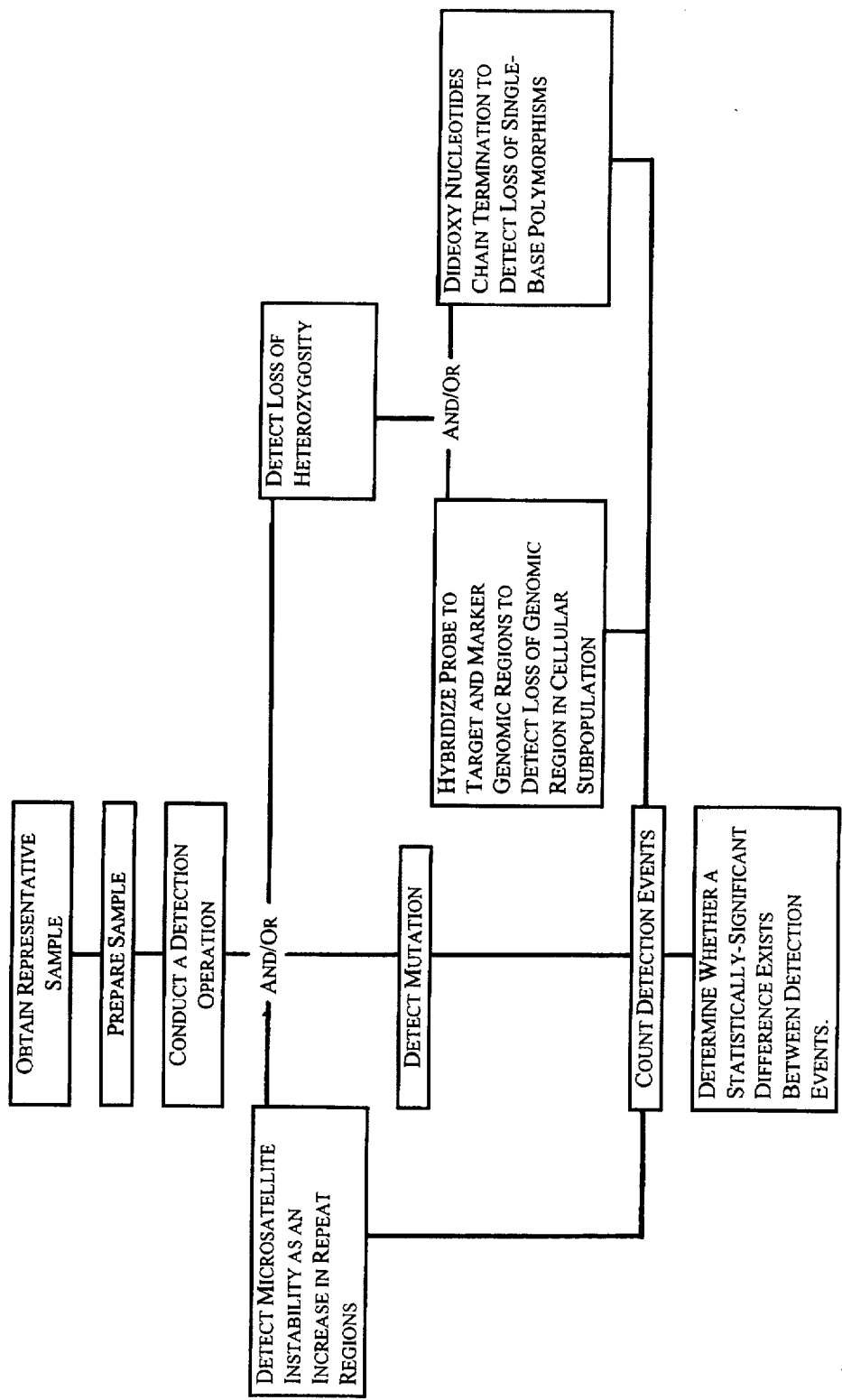
FIG. 1 is a flow chart showing sequential steps in methods of the invention.

Methods according to the present invention are useful for the detection of genomic instability in a heterogeneous cellular sample in which the genomic instability occurs in only a small subpopulation of cells in the sample. Using traditional detection methods, such a subpopulation would be difficult, if not impossible, to detect especially if the mutation that is causative of genomic instability is unknown at the time of detection or a clonally-impure cellular population is used. See, e.g., U.S. Pat. No. 5,527,676 (reporting that a clonal population of cells should be used in order to detect a deletion in a p53 gene). Traditional methods for detection of mutations involved in carcinogenesis rely upon the use of a clonally-pure population of cells and such methods are best at detecting mutations that occur at known "hot spots" in oncogenes, such as k-ras. See, Sidransky, supra. Using the PCR-based methods of the art, an extremely large number of primers would have to be designed and sample would have to be tested numerous times to detect genomic instability in a cellular sample that is clonally-impure (i.e., a heterogeneous sample such as stool) and in which the mutation to be detected is unknown and exists in a very small number of cells. Moreover, PCR is not useful for detection of the absence of a genetic sequence, as in the case of the present methods for detecting loss of heterozygosity. Even after such repeated testing, a PCR-based method may not detect a mutation in a small number of cells in a clonally-impure population if, for example, primers bordering the site of the mutation are not used. Thus, in early-stage adenomas (when the population of mutated cells is very small), methods of the art are, at best, impractical and may not work at all.

In contrast, methods of the present invention are capable of detecting genomic instability in a small number of cells in an impure cellular population because such methods do not rely upon knowing which mutation exists and such methods are not affected by the presence in the sample of heterogeneous DNA. For example, in loss of heterozygosity, deletions occur over large portions of the genomes and entire alleles may be missing (or at least enough of an allele may be missing in order to render the allele non-functional). Methods of the invention comprise counting a number of a gene suspected of being mutated and comparing that number with the number of a gene known not to be mutated in the same sample. All that one needs to know is at least a portion of the sequence of a wild-type gene in which the mutation is suspected to occur and at least a portion of the wild-type sequence of a reference gene in which mutation is not suspected to have occurred.

Accordingly, methods of the present invention are useful for the detection of changes in a genomic nucleotide sequence present in a subpopulation of cells or debris therefrom in a sample. Such changes generally occur as a mutation (i.e., a substitution, modification, deletion, addition, or rearrangement) in a wild-type allelic sequence in a subpopulation of cells. In the case of a tumor suppressor gene, the mutation typically takes the form of a massive deletion characteristic of loss of heterozygosity. Often, as in the case of certain forms of cancer, disease-causing mutations initially occur in a single cell which then produces a small subpopulation of mutant cells. By the time clinical manifestations of the mutation are detected, the disease may have progressed to an incurable stage. Methods of the invention allow detection of a mutation when the mutation exists as only a small percentage of the total cells or cellular debris in a sample.

Methods of the invention comprise a comparison of two wild-type sequences that are expected to be present in the sample in equal numbers in normal (non-mutated) cells. In a preferred embodiment, the comparison is between (1) an amount of a genomic polynucleotide segment that is known or suspected not to be mutated in cells of the sample (the "reference") and (2) an amount of a wild-type (non-mutated) genomic polynucleotide segment suspected of being mutated in a subpopulation of cells in the sample (the "target"). A statistically-significant difference between the amounts of the two genomic polynucleotide segments indicates that a mutation has occurred. Specifically, in the case of a deletion in a tumor suppressor gene, the detected amount of the reference gene is significantly greater than the detected amount of the target gene. If a target sequence is amplified, as in the case of certain oncogene mutations, the detected amount of target is greater than the detected amount of the reference gene by a statistically-significant margin.

Methods according to the art generally require the use of numerous probes, usually in the form of PCR primers and/or hybridization probes, in order to detect a deletion or a point mutation. However, because methods of the present invention involve quantitative detection of nucleotide sequences and quantitative comparisons between sequences that are known to be stable and those that are suspected of being unstable, only a few probes must be used in order to accurately assess cancer risk. In fact, a single set (pair) of probes is all that is necessary. The risk of cancer is indicated by the presence of a mutation in a genetic region known or suspected to be involved in oncogenesis. Patients who are identified as being at risk based upon tests conducted according to methods of the invention are then directed to other, typically invasive, procedures for confirmation and/or treatment of the disease.

Quantitative sampling of a nucleotide sequence that is uniformly distributed in a biological sample typically follows a Poisson distribution. For large populations, such as the typical number of genomic polynucleotide segments in a biological sample, the Poisson distribution is similar to a normal (Gaussian) curve with a mean, N, and a standard deviation that may be approximated as the square root of N.

Statistical-significance between numbers of target and reference genes obtained from a biological sample may be determined by any appropriate method. See, e.g., Steel, et al., Principles and Procedures of Statistics, A Biometrical Approach (McGraw-Hill, 1980), the disclosure of which is incorporated by reference herein. An exemplary method is to determine, based upon a desired level of specificity (tolerance of false positives) and sensitivity (tolerance of false negatives) and within a selected level of confidence, the difference between numbers of target and reference genes that must be obtained in order to reach a chosen level of statistical significance. A threshold issue in such a determination is the minimum number, N, of genes (for each of target and reference) that must be available in a population in order to allow a determination of statistical significance. The number N will depend upon the assumption of a minimum number of mutant alleles in a sample containing mutant alleles (assumed herein to be at least 1%) and the further assumption that normal samples contain no mutant alleles. It is also assumed that a threshold differences between the numbers of reference and target genes must be at least 0.5% for a diagnosis that there is a mutation present in a subpopulation of cells in the sample. Based upon the foregoing assumptions, it is possible to determine how large N must be so that a detected difference between numbers of mutant and reference alleles of less than 0.5% is truly a negative (i.e. no mutant subpopulation in the sample) result 99.9% of the time.

Figure 4A:
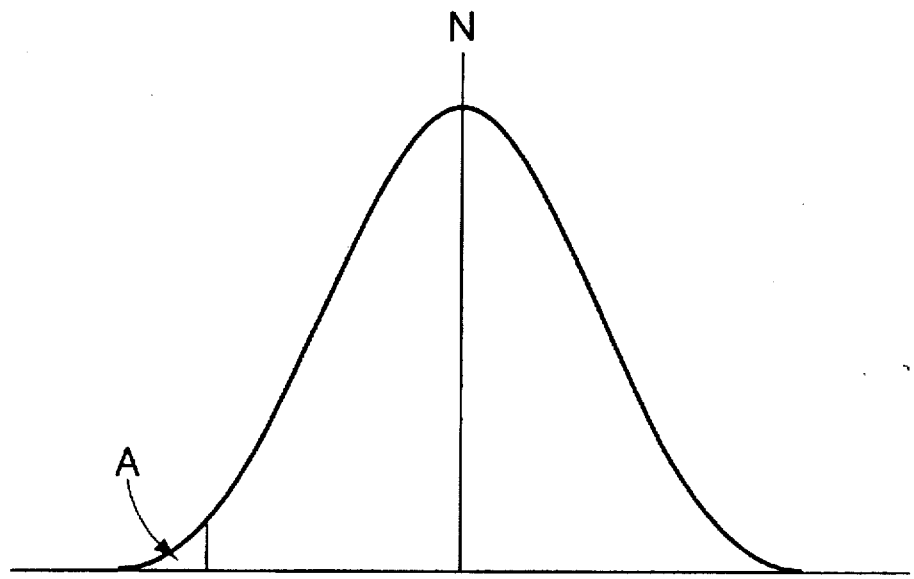
FIGS. 4A and 4B are model Gaussian distributions showing regions of low statistical probability.
Figure 4B:
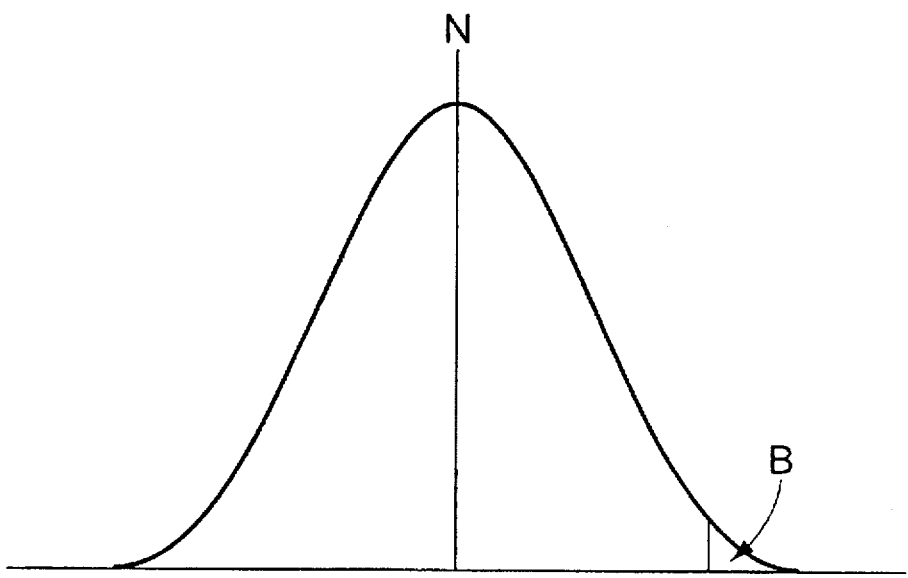

The calculation of N for specificity, then, is based upon the probability of one sample measurement being in the portion of the Gaussian distribution covering the lowest 3.16% of the population (the area marked "A" in FIG. 4A) and the probability that the other sample measurement is in the portion of the Gaussian distributioncovering the highest 3.16% of the population (the area marked "B" in FIG. 4B). Since the two sample measurements are independent events, the probability of both events occurring simultaneously is approximately 0.001 or 0.1%. Thus, 93.68% of the Gaussian distribution (100%–2×3.16%) lies between the areas marked A and B in FIG. 5. Statistical tables indicate that such area is equivalent to 3.72 standard deviations. Accordingly, 0.5%N equals 3.72 sigma. Since sigma (the standard deviation) is equal to $\sqrt{N}$, the equation may be solved for N as 553,536. This means that if the lower of the two numbers representing reference and target is at least 553,536 and if the patient is normal, the difference between the numbers will be less than 0.5% about 99.9% of the time.

Figure 5:
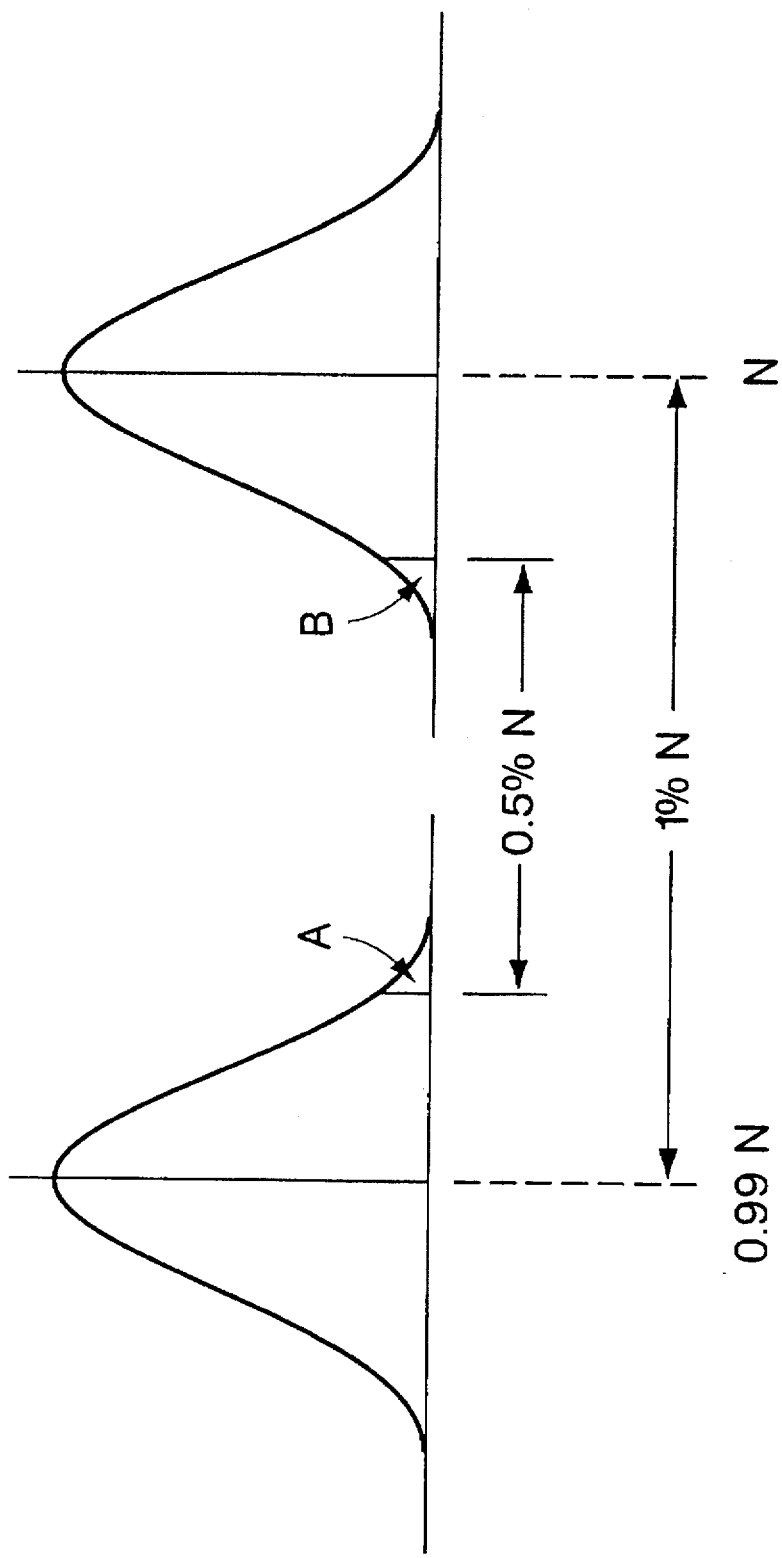
FIG. 5 is graph showing the probable values of N for a heterogeneous population of cells in which 1% of the cells are mutated.

To determine the minimum N required for 99% sensitivity a similar analysis is performed. This time, one-tailed Gaussian distribution tables show that 1.28 standard deviations (sigma) from the mean cover 90% of the Gaussian distribution. Moreover, there is a 10% (the square root of 1%) probability of one of the numbers (reference or target) being in either the area marked "A" in FIG. 5 or in the area marked "B" in FIG. 5. If the two population means are a total of 1% different and if there must be a 0.5% difference between the number of target and reference genes, then the distance from either mean to the threshold for statistical significance is equivalent to 0.25%N (See FIG. 5) for 99% sensitivity. As shown in FIG. 5, 0.25%N corresponds to about 40% of one side of the Gaussian distribution. One-tailed statistical tables reveal that 40% of the Gaussian distribution corresponds to 1.28 standard deviations. Therefore, 1.28 sigma is equal to 0.0025N, and N equals 262,144. Thus, for abnormal samples, the difference will exceed 0.5% at least 99% of the time if the lower of the two numbers is at least 262,144. Conversely, an erroneous negative diagnosis will be made only 1% of the time under these conditions.

In order to have both 99.9% specificity (avoidance of false positives) and 99% sensitivity (avoidance of false negatives), a sample with at least 553,536 (or roughly greater than 550,000) of both target and reference alleles should be used. A difference of at least 0.5% between the numbers obtained is significant at a confidence level of 99.0% for sensitivity and a difference of less than 0.5% between the numbers is significant at a confidence level of 99.9% for specificity. As noted above, other standard statistical tests may be used in order to determine statistical significance and the foregoing represents one such test.

Based upon the foregoing explanation, the skilled artisan appreciates that methods of the invention are useful to detect mutations in a subpopulation of a polynucleotides in any biological sample. For example, methods disclosed herein may be used to detect allelic loss (the loss of heterozygosity) associated with diseases such as cancer. Additionally, methods of the invention may be used to detect a deletion or a base substitution mutation causative of a metabolic error, such as complete or partial loss of enzyme activity. For purposes of exemplification, the following provides details of the use of methods according to the present invention in colon cancer detection. Inventive methods are especially useful in the early detection of a mutation (and especially a large deletion typical of loss of heterozygosity) in a tumor suppressor gene. Accordingly, while exemplified in the following manner, the invention is not so limited and the skilled artisan will appreciate its wide range of applicability upon consideration thereof.

Methods according to the invention preferably comprise one of three types of detection regimens. In a first preferred detection regimen, an amount of a polynucleotide known or suspected to be mutated is compared to an amount of a reference polynucleotide known or suspected not to be mutated. In a second preferred detection regimen, an amount of a polymorphic nucleotide on a maternal allele is compared to an amount of the corresponding polymorphic nucleotide on the corresponding paternal allele. Finally, a third detection regimen comprises a comparison of a microsatellite repeat region in a normal allele with the corresponding microsatellite region in an allele known or suspected to be mutated. All three exemplary detection means comprise determining whether a difference exists between the amounts of each nucleic acid being measured. The presence of a statistically-significant difference is indicative that a mutation has occurred in one of the nucleic acids being measured. Thus, methods described below are generally applicable to all forms of the invention, the variations of which are shown in FIG. 1.

I. Preparation of a Stool Sample

A sample prepared from stool voided by a patient should comprise at least a cross-section of the voided stool. As noted above, stool is not homogenous with respect to sloughed cells. As stool passes through the colon, it absorbs sloughed cells from regions of the colonic epithelium with which it makes contacts. Thus, sloughed cells from a polyp are absorbed on only one surface of the forming stool (except near the cecum where stool is still liquid and is homogenized by Intestinal Peristalsis). Taking a representative sample of stool (i.e., at least a cross-section) and homogenizing it ensures that sloughed cells from all epithelial surfaces of the colon will be present for analysis in the processed stool sample. Stool is voided into a receptacle that is preferably small enough to be transported to a testing facility. The receptacle may be fitted to a conventional toilet such that the receptacle accepts stool voided in a conventional manner. The receptacle may comprise a mesh or a screen of sufficient size and placement such that stool is retained while urine is allowed to pass through the mesh or screen and into the toilet. The receptacle may additionally comprise means for homogenizing voided stool. Moreover, the receptacle may comprise means for introducing homogenization buffer or one or more preservatives, such as alcohol or a high salt concentration solution, in order to neutralize bacteria present in the stool sample and to inhibit degradation of DNA.

The receptacle, whether adapted to fit a toilet or simply adapted for receiving the voided stool sample, preferably has sealing means sufficient to contain the voided stool sample and any solution added thereto and to prevent the emanation of odors. The receptacle may have a support frame which is placed directly over a toilet bowl. The support frame has attached thereto an articulating cover which may be placed in a raised position, for depositing of sample or a closed position (not shown) for sealing voided stool within the receptacle. The support frame additionally has a central opening traversing from a top surface through to a bottom surface of the support frame. The bottom surface directly communicates with a top surface of the toilet. Extending from the bottom surface of the support frame and encompassing the entire circumference of the central opening is a means for capturing voided stool. The means for capturing voided stool may be fixedly attached to the support frame or may be removably attached for removal subsequent to deposition of stool.

Once obtained, the stool sample is homogenized in an appropriate buffer, such as phosphate buffered saline or a chaotropic salt solution. Homogenization means and materials for homogenization are generally known in the art. See, e.g., U.S. Pat. No. 4,101,279. Thus, particular homogenization methods may be selected by the skilled artisan. Methods for further processing and analysis of a biological sample, such as a stool sample are presented below.

II. Methods for Detection of Colon Cancer or Precancer

A. Reference-Target

For exemplification, methods of the invention are used to detect a deletion or other mutation in the p53 tumor suppressor gene in cells obtained from a representative stool sample. The p53 gene is a good choice because the loss of heterozygosity in p53 is often associated with colorectal cancer. An mRNA sequence corresponding to the DNA coding region for p53 is reported as GenBank Accession No. M92424. The skilled artisan understands that methods described herein may be used to detect mutations in any gene and that detection of a p53 deletion is exemplary of such methods. At least a cross-section of a voided stool sample is obtained and prepared as described immediately above. DNA or RNA may optionally be isolated from the sample according to methods known in the art. See, Smith-Ravin, et al., *Gut*, 36:81–86 (1995), incorporated by reference herein. However, methods of the invention may be performed on unprocessed stool.

Nucleic acids may be sheared or cut into small fragments by, for example, restriction digestion. The size of nucleic acid fragments produced is not critical, subject to the limitations described below. A target allele that is suspected of being mutated (p53 in this example) and a reference allele are chosen. A reference allele may be any allele known or suspected not to be mutated in colon cancer cells. Single-stranded nucleic acid fragments may be prepared using well-known methods. See, e.g., Sambrook, et al., *Molecular Cloning, A Laboratory Manual* (1989) incorporated by reference herein.

Either portions of a coding strand or its complement may be detected in methods according to the invention. For exemplification, detection of the coding strand of p53 and reference allele are described. Complement to both p53 and reference allele are removed by hybridization to anti-complement oligonucleotide probes (isolation probes) and subsequent removal of duplex formed thereby. Methods for removal of complement strands from a mixture of single-stranded oligonucleotides are known in the art and include techniques such as affinity chromatography. Upon converting double-stranded DNA to single-stranded DNA, sample is passed through an affinity column comprising bound isolation probe that is complementary to the sequence to be isolated away from the sample. Conventional column chromatography is appropriate for isolation of complement. An affinity column packed with sepharose or any other appropriate materials with attached complementary nucleotides may be used to isolate complement DNA in the column, while allowing DNA to be analyzed to pass through the column. See Sambrook, Supra. As an alternative, isolation beads may be used to exclude complement as discussed in detail below.

After removal of complement strands, first oligonucleotide probes which hybridize to at least a portion of the p53 allele and second oligonucleotide probes that hybridize to at least a portion of the reference allele are obtained. The probes are labeled with a detectable label, such as fluorescein or detectable particles. Distinct labels for the probes are preferred.

Labeled probes are then exposed to sample under hybridization conditions. Such conditions are well-known in the art. See, e.g., Wallace, et al., *Nucleic Acids Res.*, 6:3543–3557 (1979), incorporated by reference herein. First and Second oligonucleotide probes that are distinctly labeled (i.e. with different radioactive isotopes, fluorescent means, or with beads of different size. See infra) are applied to a single aliquot of sample. After exposure of the probes to sample under hybridization conditions, sample is washed to remove any unhybridized probe. Thereafter, hybridized probes are detected separately for p53 hybrids and reference allele hybrids. Standards may be used to establish background and to equilibrate results. Also, if differential fluorescent labels are used, the number of probes may be determined by counting differential fluorescent events in a sample that has been diluted sufficiently to enable detection of single fluorescent events in the sample. Duplicate samples may be analyzed in order to confirm the accuracy of results obtained.

If there is a statistically-significant difference between the amount of p53 detected and the amount of the reference allele detected, it may be assumed that a mutation has occurred in p53 and the patient is at risk for developing or has developed colon cancer. Statistical significance may be determined by any known method. A preferred method is outlined above.

The determination of a p53 mutation allows a clinician to recommend further treatment, such as endoscopy procedures, in order to further diagnose and, if necessary, treat the patient's condition. The following examples illustrate methods of the invention that allow direct quantification of hybridization events.

1. Method for Increased Quantitation of Target and Reference Polynucleotides

Enhanced quantification of binding events between hybridization probes and target or reference is accomplished by coupling hybridization probes to particles, such as beads (hybridization beads).

In order to obtain a precise quantitative measure of the amount of a polynucleotide in a sample, hybridization beads are constructed prior to conducting hybridizations, such that each bead has attached thereto a single oligonucleotide probe.

a. Method for Preparation of Probe-Bead Combinations

A single probe is attached to a bead by incubating a large excess of hybridization beads with oligonucleotide probes of a given type (i.e., either first or second oligonucleotide probes). Coupling of probe to bead is accomplished using an affinity-binding pair. For example, beads may be coated with avidin or streptavidin and probes may be labeled with biotin to effect attachment of the probe to the bead. The mixture of beads and probes is agitated such that virtually 100% of the probes are bound to beads. The mixture is then exposed to a matrix, such as an affinity column or a membrane coated with oligonucleotides that are complementary to the probe. Only beads that have an attached probe will adhere to the matrix, the rest being washed away. Beads with coupled probe are then released from the matrix by melting hybridizations between probe and complement. Multiple exposures to the matrix and pre-washing of the column reduces non-specific binding. Moreover, naked beads (i.e., without attached probe) may be exposed to the matrix to determine a background number of beads that can be expected to attach to the matrix in the absence of probe.

By using a vast excess of beads relative to probe as described above, it is expected that the vast majority of recovered beads will have only one attached probe. For example, if a mixture has a ratio of 1 probe to 1000 beads, it is expected that only about 1 bead in a million will have two attached probes and even less than one bead in a million will have more than two attached probes. Accordingly, hybridization beads are provided in an effective 1:1 ratio with probe which allows for precise quantification of target and reference polynucleotide as described below.

For each assay described below, two distinct hybridization beads are used. A first hybridization bead has attached thereto a single first oligonucleotide probe that is complementary to at least a portion of a target polynucleotide (e.g., a p53 allele). A second hybridization bead, of a size distinct from the first hybridization bead, has attached thereto a single second oligonucleotide probe that is complementary to at least a portion of a reference polynucleotide (i.e., one that is known or suspected not to be mutated in the sample).

b. Use of Beads to Quantify Target Reference Polynucleotides

DNA is melted (denatured to form single-stranded DNA) by well-known methods See, e.g., Gyllensten, et al., in *Recombinant DNA Methodology II*, 565–578 (Wu, ed., 1995), incorporated by reference herein. According to methods of the invention, one may detect either a coding strand or its complement in order to quantify target and/or reference polynucleotide. For purposes of illustration, the present example assumes detection of the coding strand.

2. Removal of Complement

Single-stranded complement of the target polynucleotide (e.g., p53) and reference polynucleotide are removed from the sample by binding to oligonucleotide probes that are complementary to target or reference complement. Such probes, referred to herein as isolation probes, are attached to isolation beads prior to their introduction into the sample. The beads may be magnetized. Thus, when magnetized isolation beads [with attached isolation probe(s)] are introduced into the sample, the attached isolation probes hybridize to complement of target or reference (or vice versa). Isolation beads are preferably introduced in vast excess in order to saturate complement binding. Once hybridization is complete, a magnetic field is applied to the sample, thus drawing the magnetized isolation beads (both with and without hybridized complement) out of the sample. Assuming that a sufficient quantity of isolation beads are introduced into the sample, removal of the isolation beads effectively removes all target and reference complement from the sample. In an alternative embodiment for complement removal, an excess of oligonucleotide probe with attached biotin is exposed to the dehybridized sample under hybridization conditions. Once hybridization is complete the sample is exposed to a column lined with avidin. The biotin-bound probe, whether free or hybridized to complement, is bound by avidin on the column. The remainder of the DNA, including target and reference coding strands to be detected, is passed through the column. In contrast to the description of hybridization beads above, beads for removal of complement may be constructed so numerous oligonucleotides are bound to a single bead.

3. Detection and Quantitation of Target and Reference

Two sets of hybridization beads are prepared as described above. Each member of a first set of hybridization beads (all of which are identical to each other) has attached thereto a single oligonucleotide probe that is complementary to at least a portion of the target polynucleotide. Each member of a second set of identical hybridization beads (all of which are identical to each other but not to the first set) has attached thereto a single oligonucleotide probe that is complementary to at least a portion of the reference polynucleotide. Members of the second set of hybridization beads are of a size or color distinct from that of members of the first set of hybridization beads. First and second hybridization beads may also be distinguished on the basis of other characteristics. For example, beads may have attached fluorescent markers that are distinguished by their fluorescence at different wavelengths. Beads with distinct electrochemical charges may also be used. The precise modality used for distinguishing beads is not essential to the invention as long as it is possible to distinguish between first and second probe on the basis of distinctions between attached first and second beads.

Both sets of hybridization beads with attached probes are exposed to the sample under hybridization conditions, thereby allowing attached probe to hybridize to reference or target. Once hybridization is complete, the sample is washed to remove unhybridized bead/probe combinations. Unhybridized bead/probe combinations are removed by, for example, passing the sample through a column comprising DNA complementary to the probe sequence. Thus, any unhybridized bead/probe combinations are retained on the column while duplex is passed through the column. Subsequently, the sample is exposed to means for differentially counting hybridization beads in order to quantify first and second hybridization probes which have formed duplexes. The numbers obtained provide a precise estimate of the number of copies of the reference and target polynucleotide in the population because differential counting means count individual beads. One bead is equal to one probe which, in turn, signifies one copy of the nucleic acid being measured.

Figure 2:
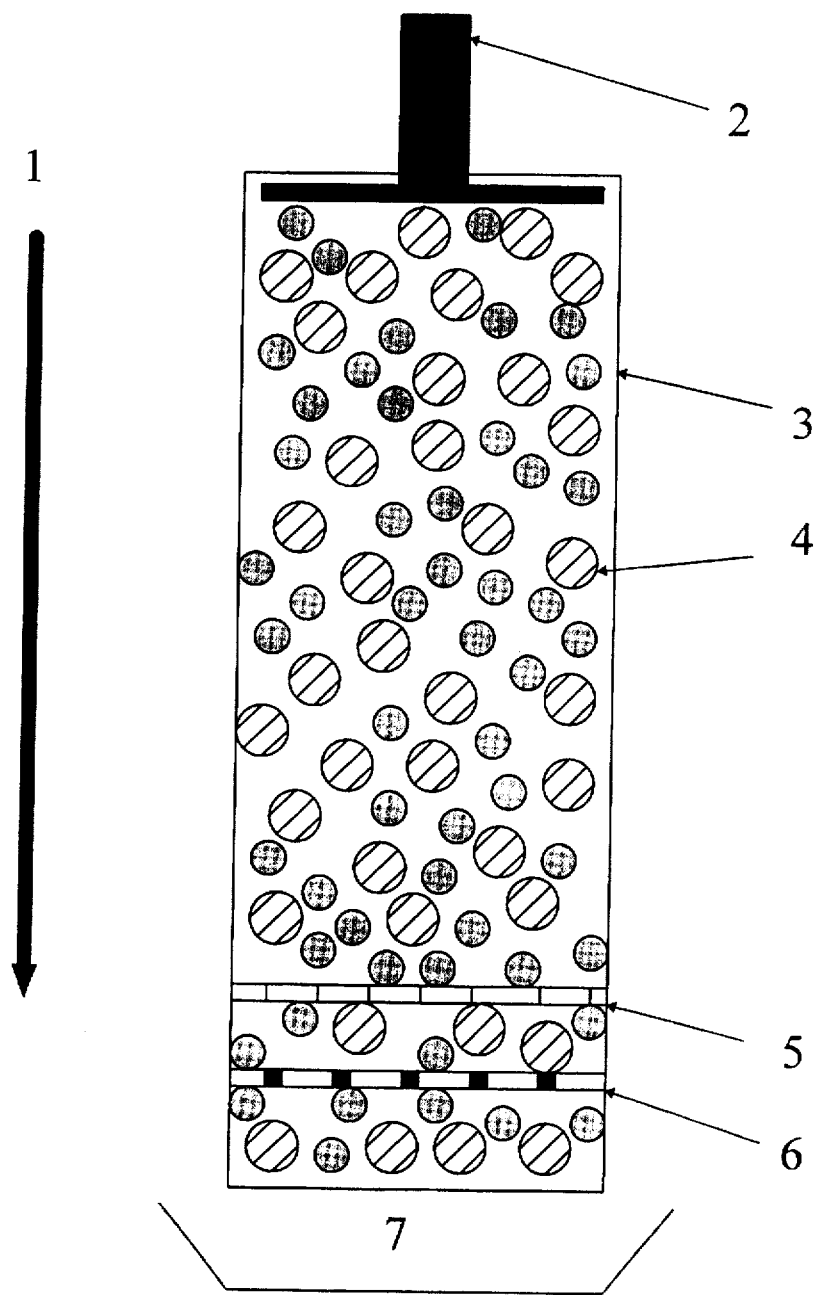
FIG. 2 is a schematic diagram of a multi-orifice impedance counter of the type useful in accordance with the invention to count hybridization events; wherein reference numeral 1 indicates the direction of flow through the column; reference numeral 2 indicates a plunger means for forcing material downward in the column; reference numerals 3 and 4 are different-sized hybridization beads; reference numeral 5 is an optional filter for extracting unwanted particles; reference numeral 6 indicates an array of orifices for measuring differential impedance; and reference numeral 7 is a collection chamber.

An example of a differential counting means is an impedance measuring device, such as a Coulter counter (Coulter Electronics, Inc., Miami, Fla.). Sample is passed through the device which differentially detects the two types of hybridization beads by measuring their differential impedance of an electric current. Alternatively, the device may measure fluorescent, color, or other changes. In order to increase the speed of the assay, a multi-orifice device may be used. A multi-orifice impedance counter is shown schematically in FIG. 2. A multi-orifice array is placed at one end of a column filled with an electrically-conductive fluid, such as saline. Hybridization beads with either hybridized target or reference segments are inserted at an opposite end of the column. Each orifice is large enough to accommodate only one hybridization bead at a time and sufficiently wide to allow reliable impedance measurements. An electric voltage is passed across each orifice. Each hybridization bead (which is non-conducting), as it passes through one of the orifices, displaces a volume of saline, thus creating a brief impedance change that is proportional to the size of the bead. This, in turn, creates a measurable decrease in current that is directly correlated with the size of the bead. By compiling the number of each of the two distinct impedance events, a precise estimate of the number of hybridization beads and, therefore, the number of probes of each type in the population is obtained.

Upon quantitative measurement of first and second hybridization beads, data are analyzed as discussed above to determine whether any statistically-significant difference exists between the amounts of first and second hybridization beads (with hybridized probe attached). A statistically-significant reduction in the amount of target is indicative of a mutation in the target allele. Where the p53 gene is the target allele, such a mutation is indicative of a cancerous or precancerous condition. A clinician may use such results as a basis for prescribing additional treatment, such as endoscopy and polypectomy procedures.

B. Detection of Mutations in Single-base Polymorphisms

The basic method described above may also be applied to detect a loss of heterozygosity or other mutation at a single base polymorphic site between maternal and paternal alleles. Such detection is typically an indication of a larger deletion or other mutation. However, a mutation at a single polymorphic nucleotide may be all that is necessary to inhibit gene function in one of the two alleles. A deletion associated with loss of heterozygosity may be difficult to detect due to a recently-discovered phenomenon called complementary reduplication. In complementary reduplication, the loss of one of two alleles at a particular locus results in "reduplication" of the surviving allele. Reduplication usually takes place on the chromosome containing the surviving allele and involves the production of one or more copies of the surviving allele in close proximity on the chromosome to the position of the surviving allele. In the case of a locus that displays one or more single-base allelic polymorphisms (i.e., heterozygosity at the locus is determined by virtue of one or more single-base differences in one or more regions of the locus), complementary reduplication results in the insertion on the chromosome containing the surviving allele of a duplicate of the sequence corresponding to that which was deleted. Even under the most stringent hybridization conditions, some of a probe directed against the deleted sequence will bind to the reduplicated sequence at a locus of a single-base polymorphism. Accordingly, in such circumstances, the deletion may not be detected because any true difference in the number of probes binding to the polymorphic site (i.e., the allelic region encompassing the single-base polymorphism) may be obscured by an increase resulting from the other allele's reduplicated region.

The problems associated with complementary reduplication, and with non-specific probe binding generally, are solved by methods of the invention. Such methods allow detection of a deletion in one of two alleles present at a specific locus in a subpopulation of cells contained in a biological sample. Numerous alleles, including tumor suppressor alleles, contain single polymorphic nucleotides in the context of a constant nucleic acid region. Individuals normally may be either homozygous or heterozygous for a particular polymorphic nucleotide. Since numerous single-base polymorphic nucleotide sites exist in most alleles, the probability that a given individual is heterozygous at least one of the single-base polymorphism sites is high. A statistically-significant reduction in one of the two nucleotides at a single-base polymorphic site (at which the individual is heterozygous) is used as a marker for a deletion in the allele encompassing that site.

Genomic regions containing known single-base polymorphisms are identified by reference to a nucleotide database, such as GenBank, EMBL, or any other appropriate database. For purposes of the invention, a single-base polymorphism is intended to be a single polymorphic nucleotide adjacent to a non-polymorphic region of the allele regardless of whether the single polymorphic nucleotide forms part of a larger polymorphic site (i.e. the single-base polymorphism may be the terminal nucleotide of a larger, polynucleotide polymorphism). For cancer detection, the regions considered are regions in which loss of heterozygosity is prevalent, such as tumor suppressor genes. A given individual may be homozygous or heterozygous for the polymorphic nucleotide in any identified single-base polymorphic region. Accordingly, if a number of single-base polymorphic regions are identified, the probability increases that at least one heterozygous single-base polymorphic region is found in a sample.

Once single-base polymorphic sites are identified, a sample is obtained from a patient in order to determine which of those sites is heterozygous in normal (i.e., non-cancerous or pre-cancerous) cells. Then, sample is prepared as described above. Double-stranded DNA in the sample is converted to single-stranded DNA. Then, either the coding strand or the anti-coding strand for both alleles is isolated from the sample. As will be evident from the following discussion, methods disclosed herein are indifferent as to whether coding strand or anti-coding strand is retained in the sample.

An oligonucleotide probe is constructed that is complementary to a portion of the region of single-base polymorphism, said portion ending at the nucleotide that is immediately 3' to the polymorphic nucleotide, regardless of whether the 5'-3' (coding) strand or the 3'-5' (anticoding) strand is used as a template. FIG. 3 shows four possible probes that are immediately 3' to the polymorphic nucleotide for each of four possible template strands as described above (the Sequences in FIG. 3 are hypothetical and are not intended to represent any actual sequence). While either strand may be used as a template for probe binding to determine heterozygosity and/or the loss thereof, the sequence of the probe that is hybridized to the template will be different depending upon the strand used. Probes may be of any length that allows efficient and specific hybridization of probe to target. FIG. 3 illustrates the four probes that are useful for hybridization to the hypothetical sequence shown. The length of probe sequences may be determined as appropriate for each genomic region that is analyzed. A preferable length is between about 10 and about 100 nucleotides. The size of the probe will also depend upon the size of the region surrounding the single-base polymorphism (i.e., the region 5' or 3' to the next adjacent polymorphism, if any). Details concerning the construction and hybridization of oligonucleotide probes are known in the art.

Once constructed, unique probes for each polymorphic region will hybridize to regions of both maternal and paternal alleles up to, but not including, the polymorphic nucleotide, which, in a heterozygote, will be different in the maternal and paternal alleles. FIG. 3 illustrates the foregoing hybridization procedure. FIG. 3 shows only a small portion of the region surrounding the polymorphic nucleotide. The alleles shown in FIG. 3 are heterozygous at the polymorphic site (shown in bold type in FIG. 3).

Probe is hybridized to its specific template DNA (see above) by standard methods in the art. The sample may optionally be washed to remove unhybridized probe. To determine whether each single-base polymorphic region to which probe has bound is heterozygous or homozygous at the polymorphic nucleotide, a modification of the dideoxy chain termination method as reported in Sanger, *Proc. Nat'l Acad. Sci. (USA),* 74:5463–5467 (1977), incorporated by reference herein, is used. The method involves using at least two of the four common 2', 3'-dideoxy nucleoside triphosphates (ddATP, ddCTP, ddGTP, and ddTTP). A different detectable label is attached to each dideoxy nucleoside triphosphate (ddNTP) according to methods known in the art. Differentially-labeled ddNTPs are available from Perkin Elmer Corporation (Cat. No. 401456). At least two labeled ddNTPs then are exposed to each sample having probe hybridized to maternal and paternal alleles as described above. The choice of which two ddNTPs are used will depend upon the nucleotides at the heterozygous polymorphic site. A DNA polymerase, such as Sequenase™ (Perkin-Elmer), is also added to the sample mixture. Using the allelic strands as primer, the polymerase will add one ddNTP to the 3' end of the probe, the incorporated ddNTP being complementary to the nucleotide that exists at the single-base polymorphic site. Because the ddNTPs have no 3' hydroxyl, further elongation of the hybridized probe will not occur. After completion, the sample is washed to remove excess ddNTPs. Label is then counted in each sample. The presence of two differentially-labeled ddNTPs in a sample is indicative of heterozygosity at the polymorphic site. Any 3' modified nucleoside triphosphate may be used in the above-described methods as long as the 3' modification prevents binding of an additional 3' nucleotide (i.e. probe extension) and does not inhibit binding of the modified nucleotide to the 3' end of the probe.

It is not necessary to determine the amount of each label present in the sample in order to establish heterozygosity or homozygosity. For Example, differentially-labeled deoxynucleoside triphosphates may be used for a determination of heterozygosity or homgozygosity. The mere fact that two different labeled dideoxy nucleotides are incorporated into the probe means that the single-base polymorphic site being analyzed is heterozygous. However, determination of sites at which a patient is polymorphic is useful in order to establish a baseline of polymorphisms which may be used in future tests to detect changes in polymorphic sites which may be indicative of cancer. The existence of polymorphisms may be determined by methods taught herein, gel electrophoresis or by other standard methods.

In the case in which heterozygosity exists at the polymorphic site, counting the amount of each of the two differentially-labeled ddNTPs allows a determination of whether there is a loss of heterozygosity (i.e., a deletion) in a subpopulation of cells in the sample. In a normal (i.e., non-cancerous) sample containing cells that are heterozygous at the single-base polymorphic site, it is expected that the detected amount of each of the two ddNTPs added to the probe will be identical (within chosen limits of statistical significance). However, if a deletion has occurred in one of the two alleles in a subpopulation of cells in the sample, there will be a statistically-significant difference between the amounts of each of the two alleles detected via the incorporated (labeled) ddNTPs. The detection of such a difference is indicative of genomic instability within the sample. Such genomic instability indicates the possibility of cancerous or pre-cancerous cells in the sample.

In order to improve the ability to accurately count alleles to which ddNTPs have attached, ddNTPs are labeled with hybridization-type beads of different sizes as described above. Alleles with bound probe comprising a labeled ddNTP are counted as described above using a counting device, such as a Coulter counter. Also as described above, differential fluorescent labels or other counting means may be used to separately detect incorporated ddNTPs.

The detection of heterozygosity at single-base polymorphic sites and the detection of the loss of heterozygosity may be determined in separate steps. For example, probes may be hybridized immediately adjacent to but not including the nucleotide determined to be polymorphic as described above. The four ddNTPs may then be added to the sample, washed, and the presence or absence of each label may be detected. Detection of only one label indicates that the individual from whom the sample was obtained is homozygous at the site of the polymorphic nucleotide. Detection of two labels means that the individual is heterozygous. The heterozygous loci are noted. As noted above, baseline determinations of heterozygosity may be done using standard deoxynucleotides. Once a baseline is established, future tests on that individual are performed on the heterozygous loci in order to detect a loss of heterozygosity as described immediately above. For the detection of cancer, the heterozygous loci are typically tumor suppressor genes, including p53, dcc, apc, and others. Using methods of the invention, a "fingerprint" of heterozygous tumor suppressor loci may be constructed. Future deviation from the fingerprint (i.e., deletions) provides valuable information as to the development of cancer.

A preferred use of the foregoing methods is in the detection of colon cancer. A representative stool sample is prepared as described above. At least a cross-section of the stool sample is placed in buffer and homogenized. Double-stranded DNA is converted to single-stranded DNA and complement of the strand to be detected is removed from the sample by any of the methods described above. The remaining single-stranded DNA is exposed to multiple copies of a probe designed on the basis of known single-base polymorphisms in a cancer-associated allele, such as a tumor suppressor allele, such that the probe hybridizes with a desired number of nucleotides immediately adjacent to the polymorphic nucleotide as described above. After hybridization is complete, the sample is washed and exposed to differentially-labeled ddNTPs and a DNA polymerase. The sample is then washed to remove unincorporated ddNTPs. The presence of any labeled ddNTPs is determined. If two labels are detected, the individual from whom the sample is obtained is heterozygous at the polymorphic nucleotide. The heterozygosity of the allele and the probe sequence matching the site immediately adjacent to the polymorphic allele are noted for reference in future testing for the loss of heterozygosity. Alternatively, once the patient is determined to be heterozygous at a locus, an assay may be performed immediately in the manner described above in order to determine a present loss of heterozygosity in a subpopulation of cells in the sample.

C. Analysis of Microsatellite Instability

Microsatellites are di- or trinucleotide repeats found throughout the genome. A particular array of microsatellite repeats is often associated with a particular genomic sequence and is stably inherited under normal conditions. Expansions of microsatellite copy number typically are associated with defects in mismatch repair. Accordingly, changes in a microsatellite regions indicate that the patient is at risk for a mutation in other genomic regions, which may lead to cancer.

In order to detect microsatellite instability as an indicator of a mutation in a cancer-associated gene, one must first identify a microsatellite region associated with the gene of interest. Such regions are typically identified on a database, such as GenBank, EMBL, and others. Once a wild-type microsatellite region associated with, for example, the p53 tumor suppressor gene is identified, an oligonucleotide probe is constructed that spans the microsatellite region and the regions immediately 5' and immediately 3' to the microsatellite region. The precise length of probes may be determined by the experimenter. Probes are constructed that hybridize to the microsatellite region, including 5' and 3' extensions, on both the maternal and paternal alleles in which the microsatellite is associated with, for example, p53.

An appropriate sample of body tissue or fluid is obtained and processed as described herein. Double stranded DNA is denatured and an excess of maternal and paternal probes, as described above, are introduced into the sample under hybridization conditions. The probes are detectably labeled as described above. Complement of the strands to be detected may optionally be removed by methods described above. The sample is then washed to remove unhybridized probe and the amount of hybridized probe in quantitatively detected.

Quantitative detection may be accomplished by any means described herein. For example, probes may be attached to hybridization beads such that probes that bind to maternal allele are attached to beads of one size and probes that bind to paternal allele are attached to beads of a second size that is distinguishable from beads of the first size. Beads with attached probe may be counted as described above.

The detection of a statistically-significant difference between the amount of probe binding to the maternal allele and the amount of probe binding to the paternal allele is indicative of microsatellite instability. As previously mentioned, microsatellite instability is indicative of a mutation at the locus in which the microsatellite resides. If the microsatellite region is associated with a tumor suppressor gene or an oncogene, the detection of microsatellite instability in an allele in a subpopulation of cells in a biological sample is indicative of the potential for cancer or that cancer or precancer may have already developed. Further testing as described herein (either by invasive or noninvasive means) may then be conducted.

In an alternative embodiment, a "fingerprint" of Microsatellites is taken from regions associated with cancer-causing genes in a sample obtained from a patient. The fingerprint comprises the sequence of wild-type Microsatellites associated with the cancer-causing gene or genes. Once obtained, the fingerprint is stored and is used in future tests of samples from the same patient in order to monitor changes in microsatellite regions (i.e. microsatellite instability) that may be associated with the development of cancer. Changes in microsatellite length and/or sequence over time may be used to prescribe additional testing and/or treatment in order to detect and remove cancerous tissue at an early stage in its etiology.

The invention has been described in terms of its preferred embodiments. Numerous additional aspects and advantages by the invention are apparent to the skilled artisan upon consideration of the foregoing.

What is claimed is:

1. A method for detecting the presence of a clonal subpopulation of transformed cells in a biological sample obtained from an organism, comprising the steps of:
   a) determining from the biological sample a number X of a first wild-type polynucleotide characteristic of a genomic region of said organism that is not mutated in said subpopulation of transformed cells;
   b) determining from the biological sample a number Y of a second wild-type polynucleotide in a genomic region of said organism suspected of being mutated in said subpopulation of transformed cells; and
   c) determining whether a difference exists between number X and number Y,
      the presence of a statistically-significant difference being indicative of a clonal subpopulation of transformed cells in said biological sample.

2. The method according to claim 1, wherein said transformed cells are malignant.

3. The method according to claim 1, wherein said biological sample is selected from the group consisting of pus, sputum, semen, urine, blood, saliva, cerebrospinal fluid and biopsy tissue.

4. The method according to claim 1, wherein said biological sample is a stool sample.

5. The method according to claim 1, wherein step a) comprises exposing said biological sample to a first oligonucleotide probe having a nucleotide sequence complementary to at least a portion of nucleotide sequence of said first polynucleotide.

6. The method according to claim 5, wherein said first oligonucleotide probe is detectably labeled.

7. The method according to claim 5, wherein said number x is proportional to the number of said first oligonucleotide probes that forms duplex with said first polynucleotide.

8. The method according to claim 1, wherein step b) comprises exposing said biological sample to a second oligonucleotide probe having a nucleotide sequence complementary to at least a portion of said second polynucleotide.

9. The method according to claim 8, where said number y is proportional to a number of said second oligonucleotide probes that forms duplex with said second polynucleotide.

10. The method according to claim 8, wherein said second oligonucleotide probe is detectably labeled.

11. A method for detecting the presence of a colorectal cancer or precancerous lesion in a mammalian tissue or body fluid sample, comprising the steps of:
   (a) exposing the sample to a plurality of a first oligonucleotide probe and to a plurality of a second oligonucleotide probe under hybridization conditions, thereby to hybridize
      (1) said first oligonucleotide probes to copies of a first polynucleotide segment characteristic of wild-type cells of the organism, and
      (2) said second oligonucleotide probes to copies of a second polynucleotide segment characteristic of a wild-type genomic region suspected to be deleted or mutated in colorectal cancer cells;
   (b) detecting a first number of duplexes formed between said first probe and said first segment and a second number of duplexes formed between said second probe and said second segment; and
   (c) determining whether there is a difference between the number of duplexes formed between said first probe and said first segment and the number of duplexes formed between said second probe and said second segment, the presence of a statistically-significant difference being indicative of the presence in said sample of a colorectal cancer or precancerous lesion.

12. The method according to claim 11, wherein said first and second oligonucleotide probes each are coupled to a distinct detectable label.

13. The method according to claim 11, wherein
said first oligonucleotide probes are attached to a first particle in a ratio of one first oligonucleotide probe to one particle and said second oligonucleotide probes are attached to a second particle detectably distinct from said first particle in a ratio of one second oligonucleotide probe to one second particle, wherein
said detecting step comprises separating hybridized from unhybridized first and second oligonucleotide probes and subsequently passing hybridized first and second oligonucleotide probes through a detector to determine said first and second numbers.

14. The method of claim 13, wherein said first and second particles are of detectably different sizes.

15. The method according to claim 13, wherein said first and second particles are of detectably different colors.

16. The method according to claim 11, further comprising, prior to step a) the steps of converting double-stranded DNA in said sample to single-stranded DNA and removing complement to said first and second polynucleotide segments.

17. The method according to claim 16, wherein said removing step comprises hybridizing said complement to a nucleic acid probe attached to a magnetic particle and subsequently removing said magnetic particle from the sample.

18. A method for detecting a nucleic acid sequence change in a target allele in a subpopulation of cells in a biological sample, comprising the steps of:
   (a) determining
      (i) an amount of wild-type target allele in the biological sample, and
      (ii) an amount of a reference allele in the biological sample; and
   (b) detecting a nucleic acid sequence change in the target allele in a subpopulation of cells in the biological sample as
   a statistically significant difference in the amount of wild-type target allele and the amount of reference allele obtained in said determining step.

19. The method according to claim 18, wherein said determining step comprises exposing said biological sample to a first oligonucleotide probe which hybridizes with a portion of said wild-type allele and to a second oligonucleotide probe capable of hybridizing to a portion of said reference allele, and removing from said biological sample any unhybridized first or second oligonucleotide probe.

20. The method according to claim 18, wherein said biological sample is stool.

21. The method according to claim 18, wherein said target allele is a tumor suppressor allele.

22. The method according to claim 18, wherein said tumor suppressor allele is a p53 allele.

23. A method for detecting a change in the nucleotide sequence in a subpopulation of a target allele in a heterogeneous sample of cellular material, comprising the steps of:
   a) exposing the heterogeneous sample, under hybridization conditions, to a plurality of isolation probes, each of which hybridizes to at least a portion of only one member selected from a first group consisting of a coding strand of said target allele and complement of a coding strand of said target allele;
   b) exposing the heterogeneous sample, under hybridization conditions, to a plurality of second isolation probes, each of which hybridizes to at least a portion of only one member selected from a second group consisting of a coding strand of a reference allele and a complement of a coding strand of said reference allele;
   c) contacting said heterogeneous sample, under hybridization conditions, with a plurality of first hybridization probes, each of which hybridizes to at least a portion of the member of said first group to which said first isolation probe does not hybridize;
   d) contacting the heterogeneous sample, under hybridization conditions, with a plurality of second hybridization probes, each of which hybridizes with at least a portion of the member of said second group to which said second isolation probe does not hybridize;
   e) removing non-hybridizing first and second hybridization probes from said heterogeneous sample;
   f) determining an amount of each of said first and second hybridization probes remaining in the heterogeneous sample after said removing step; and
   g) detecting allelic loss in a subpopulation of target allele as a statistically-significant difference in the amount of said first hybridization probe and said second hybridization probe obtained in said determining step.

24. The method according to claim 23, wherein said first and second hybridization probes are differentially labeled.

25. The method according to claim 23, wherein said first and second hybridization probes are attached to first and second hybridization beads, respectively, in a ratio of one probe to one bead.

26. The method according to claim 25, wherein said first hybridization beads are of a size distinct from said second hybridization beads.

27. The method according to claim 26, wherein said detecting step comprises passing said first and second hybridization beads through a Coulter counter.

28. The method according to claim 23, wherein said target allele is an allele, the mutation of which is associated with disease.

29. The method according to claim 28, wherein said disease is cancer.

30. The method according to claim 28, wherein said sample of cellular material is a stool sample obtained from a patient.

31. The method according to claim 30, further comprising the step of performing an endoscopy procedure on a patient in whose stool sample allelic loss is detected.

32. A method for detecting a deletion in polymorphic locus in a subpopulation of cells in a biological sample, comprising the steps of:
   a) detecting an amount of a maternal allele at a polymorphic locus in the biological sample;
   b) detecting an amount of a paternal allele at the polymorphic locus in the biological sample; and
   c) determining whether a statistically-significant difference exists between the amount of maternal allele and the amount of paternal allele at the polymorphic locus,
The presence of a statistically-significant difference being indicative of a deletion at the polymorphic locus in a subpopulation of cells in the biological sample.

33. The method according to claim 32, wherein said polymorphic locus is a single base polymorphism and is heterozygous between said maternal and paternal alleles.

34. The method according to claim 33, wherein said detecting steps comprise,
   a) hybridizing probe to a portion of said polymorphic locus on both maternal and paternal alleles that is immediately adjacent to said single-base polymorphism;

b) exposing said sample to a mixture of detectably-labeled dideoxy nucleotide triphosphates under conditions which allow appropriate binding of said dideoxy nucleotide triphosphates to said single-base polymorphism;

c) washing the sample; and d) counting an amount of each detectably-labeled dideoxy nucleotide triphosphate remaining for the sample.

35. The method according to claim 34, wherein said detectable label is selected from the group consisting of radioisotopes, fluorescent compounds, and particles.

36. The method according to claim 32, wherein said biological sample is selected from the group consisting of pus, blood, urine, sputum, semen, saliva, cerebrospinal fluid, biopsy tissue, and stool.

37. The method according to claim 32, wherein said polymorphic locus is identified from a database of nucleotide sequences.

38. A method for detecting heterozygosity at a single-nucleotide polymorphic locus in a biological sample, comprising the steps of:

a) hybridizing probes to a sequence immediately adjacent to a single-base polymorphism;

b) exposing the sample to a plurality of different labeled dideoxy nucleotides c) washing the sample;

d) determining which of said dideoxy nucleotides are incorporated into said probes; and e) detecting heterozygosity at the single-nucleotide polymorphic site as the detection of two dideoxy nucleotides having been incorporated into the probe.

* * * * *

Ⅰ

(12) EX PARTE REEXAMINATION CERTIFICATE (10713th)

United States Patent
Lapidus et al.

(10) Number: US 5,670,325 C1
(45) Certificate Issued: Sep. 22, 2015

(54) METHOD FOR THE DETECTION OF CLONAL POPULATIONS OF TRANSFORMED CELLS IN A GENOMICALLY HETEROGENEOUS CELLULAR SAMPLE

(75) Inventors: Stanley N. Lapidus, Bedford, NH (US); Anthony P. Shuber, Milford, MA (US); Kevin M. Ulmer, Cohasset, MA (US)

(73) Assignee: ESOTERIX GENETIC LABORATORIES, LLC, Burlington, NC (US)

Reexamination Request:
No. 90/012,806, Mar. 18, 2013
No. 90/013,251, May 29, 2014

Reexamination Certificate for:
Patent No.: 5,670,325
Issued: Sep. 23, 1997
Appl. No.: 08/700,583
Filed: Aug. 14, 1996

(51) Int. Cl.
*C12Q 1/68* (2006.01)

(52) U.S. Cl.
CPC ............ *C12Q 1/6809* (2013.01); *C12Q 1/6827* (2013.01); *C12Q 2535/125* (2013.01); *C12Q 2545/114* (2013.01); *C12Q 2600/156* (2013.01)

(58) Field of Classification Search
None
See application file for complete search history.

(56) References Cited

To view the complete listing of prior art documents cited during the proceedings for Reexamination Control Numbers 90/012,806 and 90/013,251, please refer to the USPTO's public Patent Application Information Retrieval (PAIR) system under the Display References tab.

*Primary Examiner* — Shri Ponnaluri

(57) ABSTRACT

Methods are provided for detecting the presence of mutant sequences in a subpopulation of gene sequences in a biological sample. These methods are particularly useful for identifying individuals with gene mutations indicative of early colorectal cancer.

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 11, 18, 19, 22 and 32 are determined to be patentable as amended.

Claims 2-10, 12, 20, 21, 33, 36 and 37, dependent on an amended claim, are determined to be patentable.

Claims 13-17, 23-31, 34-35 and 38 were not reexamined.

1. A method for detecting the presence of a clonal subpopulation of transformed cells in a biological sample obtained from an organism, *wherein the biological sample comprises nucleotide debris*, comprising the steps of:
   a) determining from the biological sample a number X of a first wild-type polynucleotide characteristic of a genomic region of said organism that is not mutated in said subpopulation of transformed cells, *wherein determining comprises counting the first wild-type polynucleotide in the nucleotide debris*;
   b) determining from the biological sample a number Y of a second wild-type polynucleotide in a genomic region of said organism suspected of being mutated in said subpopulation of transformed cells, *wherein determining comprises counting the second wild-type polynucleotide in the nucleotide debris*; and
   c) determining whether a difference exists between number X and number Y, the presence of a statistically-significant difference being indicative of a clonal subpopulation of transformed cells in said biological sample.

11. A method for detecting the presence of a colorectal cancer or precancerous lesion in a mammalian tissue or body fluid sample *comprising nucleotide debris*, comprising the steps of:
   (a) exposing the sample to a plurality of a first oligonucleotide probe and to a plurality of a second oligonucleotide probe under hybridization conditions, thereby to hybridize
      (1) said first oligonucleotide probes to copies of a first polynucleotide segment characteristic of wild-type cells of the organism, and
      (2) said second oligonucleotide probes to copies of a second polynucleotide segment characteristic of a wild-type genomic region suspected to be deleted or mutated in colorectal cancer cells;
   (b) detecting *in the sample* a first number of duplexes formed between said first probe and said first segment and a second number of duplexes formed between said second probe and said second segment, *wherein detecting comprises counting the first number of duplexes and the second number of duplexes in the nucleotide debris*; and
   (c) determining whether there is a difference between the number of duplexes formed between said first probe and said first segment and the number of duplexes formed between said second probe and said second segment, the presence of a statistically-significant difference being indicative of the presence in said sample of a colorectal cancer or precancerous lesion.

18. A method for detecting *the presence of* a nucleic acid sequence change in a target allele in a subpopulation of cells in a biological sample *comprising nucleotide debris*, comprising the steps of:
   (a) determining
      (i) an amount of wild-type target allele in the biological sample, *wherein determining comprises counting the amount of wild-type target allele in the nucleotide debris*, and
      (ii) an amount of a *wild-type* reference allele in the biological sample, *wherein determining comprises counting the amount of wild-type reference allele in the nucleotide debris*; and
   (b) detecting *the presence of* a nucleic acid sequence change in the target allele in a subpopulation of cells in the biological sample [as] *by way of determining* a statistically significant difference [in] *between* the amount of wild-type target allele and the amount of *wild-type* reference allele obtained in said determining step.

19. The method according to claim 18, wherein said determining step comprises exposing said biological sample to a first oligonucleotide probe which hybridizes with a portion of said wild-type allele and to a second oligonucleotide probe capable of hybridizing to a portion of said *wild-type* reference allele, and removing from said biological sample any unhybridized first or second oligonucleotide probe.

22. The method according to claim [18] *21*, wherein said tumor suppressor allele is a p53 allele.

32. A method for detecting a deletion in polymorphic locus in a subpopulation of cells in a biological sample *comprising nucleotide debris*, comprising the steps of:
   a) detecting an amount of a maternal allele at a polymorphic locus in the biological sample, *wherein detecting comprises counting the amount of maternal allele in the nucleotide debris*;
   b) detecting an amount of a paternal allele at the polymorphic locus in the *nucleotide debris of the* biological sample, *wherein detecting comprises counting the amount of paternal allele in the nucleotide debris*; and
   c) determining whether a statistically-significant difference exists between the amount of maternal allele and the amount of paternal allele at the polymorphic locus,
The presence of a statistically-significant difference being indicative of a deletion at the polymorphic locus in a subpopulation of cells in the biological sample.

* * * * *